United States Patent
King et al.

(10) Patent No.: US 11,344,382 B2
(45) Date of Patent: May 31, 2022

(54) SYSTEMS AND METHODS COMPRISING LOCALIZATION AGENTS

(71) Applicant: ELUCENT MEDICAL, INC., Brookfield, WI (US)

(72) Inventors: Laura G King, Brookfield, WI (US); Daniel W. Van Der Weide, Madison, WI (US); Fred T. Lee, Jr., Madison, WI (US)

(73) Assignee: ELUCENT MEDICAL, INC., Eden Prairie, MN (US)

( * ) Notice: Subject to any disclaimer, the term of this patent is extended or adjusted under 35 U.S.C. 154(b) by 294 days.

(21) Appl. No.: 15/113,703

(22) PCT Filed: Jan. 23, 2015

(86) PCT No.: PCT/US2015/012687
§ 371 (c)(1),
(2) Date: Jul. 22, 2016

(87) PCT Pub. No.: WO2015/112863
PCT Pub. Date: Jul. 30, 2015

(65) Prior Publication Data
US 2017/0007352 A1  Jan. 12, 2017

Related U.S. Application Data

(60) Provisional application No. 61/931,395, filed on Jan. 24, 2014.

(51) Int. Cl.
*A61B 90/00* (2016.01)
*A61B 90/98* (2016.01)
(Continued)

(52) U.S. Cl.
CPC .............. *A61B 90/39* (2016.02); *A61B 5/062* (2013.01); *A61B 5/064* (2013.01); *A61B 90/90* (2016.02);
(Continued)

(58) Field of Classification Search
CPC combination set(s) only.
See application file for complete search history.

(56) References Cited

U.S. PATENT DOCUMENTS

| | | |
|---|---|---|
| 3,689,885 A | 9/1972 | Kaplan et al. |
| 3,706,094 A | 12/1972 | Cole et al. |

(Continued)

FOREIGN PATENT DOCUMENTS

| | | |
|---|---|---|
| CN | 101069640 | 11/2007 |
| CN | 102264292 | 11/2011 |

(Continued)

OTHER PUBLICATIONS

Li et al., Radio frequency identification technology: applications, technical challenges and strategies, Management Department Journal Article, 2006, paper 34, 28 pages.

(Continued)

*Primary Examiner* — Amelie R Davis
*Assistant Examiner* — Marjan Saboktakin
(74) *Attorney, Agent, or Firm* — Casimir Jones, S.C.; Brian F. Bradley (57) ABSTRACT

Provided herein are systems and methods comprising localization agents. For example, provided herein are systems and methods for the placement of localization devices within biological systems and the detection of such localization devices for targeted surgeries or other medical procedures. For example, provided herein are systems comprising one or
(Continued)

more miniature detectable devices that are placed into a target location and activated by remote introduction of a magnetic field.

5 Claims, 3 Drawing Sheets

(51) Int. Cl.
  *A61B 90/90* (2016.01)
  *A61B 5/06* (2006.01)
(52) U.S. Cl.
  CPC ...... *A61B 90/98* (2016.02); *A61B 2090/3908* (2016.02); *A61B 2090/3929* (2016.02); *A61B 2090/3945* (2016.02); *A61B 2090/3958* (2016.02); *A61B 2090/3991* (2016.02)

(56) References Cited

U.S. PATENT DOCUMENTS

| | | | |
|---|---|---|---|
| 4,494,545 A | 1/1985 | Slocum et al. | |
| 4,561,443 A | 12/1985 | Hogrefe et al. | |
| 4,804,054 A | 2/1989 | Howson et al. | |
| 5,012,236 A | 4/1991 | Troyk et al. | |
| 5,057,095 A * | 10/1991 | Fabian | A61B 5/06 128/899 |
| 5,095,309 A | 3/1992 | Troyk et al. | |
| 5,142,292 A | 8/1992 | Chang | |
| 5,198,807 A | 3/1993 | Troyk et al. | |
| 5,221,831 A | 6/1993 | Geiszler et al. | |
| 5,241,961 A | 9/1993 | Henry | |
| 5,752,513 A | 5/1998 | Acker et al. | |
| 5,867,101 A | 2/1999 | Copeland et al. | |
| 6,020,856 A | 2/2000 | Alicot | |
| 6,026,818 A | 2/2000 | Blair et al. | |
| 6,047,214 A | 4/2000 | Mueller et al. | |
| 6,053,873 A | 4/2000 | Govari et al. | |
| 6,069,564 A | 5/2000 | Hatano et al. | |
| 6,198,963 B1 | 3/2001 | Haim et al. | |
| 6,249,212 B1 | 6/2001 | Beigel et al. | |
| 6,263,247 B1 | 7/2001 | Mueller et al. | |
| 6,361,532 B1 | 3/2002 | Burek | |
| 6,363,940 B1 | 4/2002 | Krag | |
| 6,499,488 B1 | 12/2002 | Hunter et al. | |
| 6,675,810 B2 | 1/2004 | Krag | |
| 6,698,433 B2 | 3/2004 | Krag | |
| 6,765,476 B2 | 7/2004 | Steele et al. | |
| 6,784,788 B2 | 8/2004 | Beigel et al. | |
| 6,812,842 B2 | 11/2004 | Dimmer | |
| 6,822,570 B2 | 11/2004 | Dimmer et al. | |
| 6,838,990 B2 | 1/2005 | Dimmer | |
| 6,889,833 B2 | 5/2005 | Seiler et al. | |
| 6,977,504 B2 | 12/2005 | Wright et al. | |
| 7,007,699 B2 | 3/2006 | Martinelli et al. | |
| 7,023,391 B2 | 4/2006 | Wuidart et al. | |
| 7,026,927 B2 | 4/2006 | Wright et al. | |
| 7,135,978 B2 | 11/2006 | Gisselberg et al. | |
| 7,174,201 B2 | 2/2007 | Govari et al. | |
| 7,176,798 B2 | 2/2007 | Dimmer et al. | |
| 7,289,839 B2 | 10/2007 | Dimmer et al. | |
| 7,307,530 B2 | 12/2007 | Fabian et al. | |
| 7,319,396 B2 | 1/2008 | Homanfar et al. | |
| 7,347,379 B2 | 3/2008 | Ward et al. | |
| 7,366,562 B2 | 4/2008 | Dukesherer et al. | |
| 7,407,054 B2 | 8/2008 | Seiler et al. | |
| 7,411,505 B2 | 8/2008 | Smith et al. | |
| 7,414,404 B2 | 8/2008 | Keene | |
| 7,420,468 B2 | 9/2008 | Fabian et al. | |
| 7,474,223 B2 | 1/2009 | Nycz et al. | |
| 7,518,518 B2 | 4/2009 | Homanfar et al. | |
| 7,549,960 B2 * | 6/2009 | Govari | A61B 90/39 600/437 |
| 7,558,616 B2 | 7/2009 | Govari et al. | |
| 7,575,550 B1 | 8/2009 | Govari | |
| 7,590,441 B2 | 9/2009 | Govari et al. | |
| 7,632,270 B2 | 12/2009 | Livneh | |
| 7,657,301 B2 | 2/2010 | Mate et al. | |
| 7,657,302 B2 | 2/2010 | Mate et al. | |
| 7,657,303 B2 | 2/2010 | Mate et al. | |
| 7,684,849 B2 | 3/2010 | Wright et al. | |
| 7,696,876 B2 | 4/2010 | Dimmer et al. | |
| 7,715,898 B2 | 5/2010 | Anderson | |
| 7,747,307 B2 | 6/2010 | Wright et al. | |
| 7,751,865 B2 | 7/2010 | Jascob et al. | |
| 7,778,687 B2 | 8/2010 | Dimmer et al. | |
| 7,814,916 B2 | 10/2010 | Revie et al. | |
| 7,817,040 B2 | 10/2010 | Homanfar et al. | |
| 7,818,044 B2 | 10/2010 | Dukesherer et al. | |
| 7,840,253 B2 | 11/2010 | Tremblay et al. | |
| 7,848,553 B2 | 12/2010 | Hertel et al. | |
| 7,871,423 B2 | 1/2011 | Livneh | |
| 7,899,513 B2 | 3/2011 | Phillips et al. | |
| 7,912,529 B2 | 3/2011 | Herron et al. | |
| 7,926,491 B2 | 4/2011 | Wright et al. | |
| 7,971,341 B2 | 7/2011 | Dukesherer et al. | |
| 7,993,335 B2 | 8/2011 | Rioux et al. | |
| 8,011,508 B2 | 9/2011 | Seiler et al. | |
| 8,012,154 B2 | 9/2011 | Livneh | |
| 8,057,407 B2 | 11/2011 | Martinelli et al. | |
| 8,057,468 B2 | 11/2011 | Konesky | |
| 8,100,897 B2 | 1/2012 | Zoran | |
| 8,113,210 B2 | 2/2012 | Petcavich et al. | |
| 8,114,181 B2 | 2/2012 | Gogolin | |
| 8,196,589 B2 | 6/2012 | Gisselberg et al. | |
| 8,226,640 B2 | 7/2012 | Zoran | |
| 8,239,001 B2 | 8/2012 | Verard et al. | |
| 8,271,069 B2 | 9/2012 | Jascob et al. | |
| 8,354,837 B2 | 1/2013 | Anderson | |
| 8,359,730 B2 | 1/2013 | Burg et al. | |
| 8,377,388 B2 | 2/2013 | Konesky | |
| 8,399,837 B2 | 3/2013 | Robbins et al. | |
| 8,409,190 B2 | 4/2013 | Konesky et al. | |
| 8,467,852 B2 | 6/2013 | Csavoy et al. | |
| 8,549,732 B2 | 10/2013 | Burg et al. | |
| 8,628,524 B2 | 1/2014 | Shilev | |
| 8,644,907 B2 | 2/2014 | Hartmann et al. | |
| 8,647,342 B2 | 2/2014 | Livneh | |
| 8,696,663 B2 | 4/2014 | Pardoll et al. | |
| 8,728,076 B2 | 5/2014 | Livneh | |
| 8,795,265 B2 | 8/2014 | Konesky et al. | |
| 8,795,272 B2 | 8/2014 | Rioux et al. | |
| 8,802,022 B2 | 8/2014 | Konesky | |
| 8,830,037 B2 | 9/2014 | Burke et al. | |
| 8,857,043 B2 | 10/2014 | Dimmer et al. | |
| 8,892,185 B2 | 11/2014 | Chi Sing et al. | |
| 8,939,153 B1 | 1/2015 | Reicher et al. | |
| 8,948,845 B2 | 2/2015 | Glossop et al. | |
| 8,968,171 B2 | 3/2015 | Mckenna et al. | |
| 8,973,584 B2 | 3/2015 | Brander et al. | |
| 8,979,834 B2 | 3/2015 | Zoran et al. | |
| 8,998,899 B2 | 4/2015 | Shilev et al. | |
| 9,002,434 B2 | 4/2015 | Uchiyama et al. | |
| 9,060,765 B2 | 6/2015 | Rencher et al. | |
| 9,095,333 B2 | 8/2015 | Konesky et al. | |
| 9,144,453 B2 | 9/2015 | Rencher et al. | |
| 9,234,877 B2 | 1/2016 | Hattersley et al. | |
| 9,239,314 B2 | 1/2016 | Hattersley et al. | |
| 9,730,764 B2 | 8/2017 | Van Der Weide et al. | |
| 9,987,097 B2 | 6/2018 | Derweide et al. | |
| 10,154,799 B2 | 12/2018 | Van Der Weide et al. | |
| 10,245,118 B2 | 4/2019 | Van Der Weide et al. | |
| 10,245,119 B2 | 4/2019 | Van Der Weide et al. | |
| 10,278,779 B1 | 5/2019 | Rudie et al. | |
| 2003/0018246 A1 | 1/2003 | Govari et al. | |
| 2003/0117269 A1 | 6/2003 | Dimmer | |
| 2003/0153850 A1 | 8/2003 | Davis et al. | |
| 2004/0093187 A1 | 5/2004 | Dames et al. | |
| 2004/0123871 A1 | 7/2004 | Wright et al. | |
| 2004/0169505 A1 | 9/2004 | Alun et al. | |
| 2004/0199067 A1 * | 10/2004 | Bock | G01R 33/287 600/411 |
| 2006/0093089 A1 | 5/2006 | Vertatschitsch et al. | |

(56) References Cited

U.S. PATENT DOCUMENTS

| | | | |
|---|---|---|---|
| 2006/0122007 A1* | 6/2006 | Savarese | A63B 37/0003 473/351 |
| 2007/0135803 A1 | 6/2007 | Belson | |
| 2007/0232882 A1 | 10/2007 | Glossop et al. | |
| 2008/0125630 A1 | 5/2008 | Caylor | |
| 2008/0132860 A1 | 6/2008 | Smith et al. | |
| 2008/0194912 A1 | 8/2008 | Trovato et al. | |
| 2008/0213382 A1 | 9/2008 | Ivkov et al. | |
| 2008/0281190 A1 | 11/2008 | Petcavich et al. | |
| 2009/0009335 A1 | 1/2009 | Stewart et al. | |
| 2009/0281419 A1 | 11/2009 | Troesken et al. | |
| 2010/0004523 A1 | 1/2010 | August et al. | |
| 2010/0274145 A1 | 10/2010 | Turin et al. | |
| 2010/0275934 A1 | 11/2010 | Keren | |
| 2010/0305430 A1 | 12/2010 | Troesken et al. | |
| 2011/0152673 A1 | 6/2011 | Doerr et al. | |
| 2011/0152677 A1 | 6/2011 | Faul | |
| 2011/0201923 A1 | 8/2011 | Shen | |
| 2011/0278948 A1 | 11/2011 | Forsell | |
| 2012/0082342 A1 | 4/2012 | Kim et al. | |
| 2013/0052953 A1 | 2/2013 | Rofougaran | |
| 2013/0237982 A1 | 9/2013 | Rencher et al. | |
| 2013/0345561 A1 | 12/2013 | Quigley | |
| 2014/0018663 A1 | 1/2014 | Harmer et al. | |
| 2014/0062717 A1 | 3/2014 | Mudumbai et al. | |
| 2014/0066754 A1 | 3/2014 | Chi Sing et al. | |
| 2014/0148692 A1 | 5/2014 | Hartmann et al. | |
| 2014/0309522 A1 | 10/2014 | Fullerton et al. | |
| 2015/0100109 A1 | 4/2015 | Feldman et al. | |
| 2015/0129664 A1 | 5/2015 | Brar | |
| 2015/0141811 A1 | 5/2015 | Ritchey et al. | |
| 2015/0196369 A1* | 7/2015 | Glossop | G01R 33/287 600/409 |
| 2015/0264891 A1 | 9/2015 | Brander et al. | |
| 2016/0022216 A1 | 1/2016 | Goldshtein et al. | |
| 2016/0051164 A1 | 2/2016 | Derichs et al. | |
| 2016/0192960 A1 | 7/2016 | Bueno et al. | |
| 2017/0095313 A1 | 4/2017 | Van Der Weide et al. | |
| 2017/0095315 A1 | 4/2017 | Van Der Weide et al. | |
| 2017/0238996 A1 | 8/2017 | Frame et al. | |
| 2017/0312046 A1 | 11/2017 | Van Der Weide et al. | |
| 2019/0090779 A1 | 3/2019 | Van Der Weide et al. | |
| 2019/0209263 A1 | 7/2019 | Van Der Weide et al. | |
| 2019/0239980 A1 | 8/2019 | Van Der Weide et al. | |
| 2019/0365478 A1 | 12/2019 | Rudie et al. | |
| 2019/0388178 A1 | 12/2019 | Rudie et al. | |

FOREIGN PATENT DOCUMENTS

| | | |
|---|---|---|
| DE | 10112303 | 10/2002 |
| DE | 102011006537 | 10/2012 |
| EP | 1232730 | 8/2002 |
| JP | 2005-121573 | 5/2005 |
| JP | 2005- 121573 A1 * | 12/2005 |
| JP | 2012-524627 | 10/2012 |
| WO | WO 1993/005707 | 4/1993 |
| WO | WO 2007/064013 | 6/2007 |
| WO | WO 2010/058150 | 5/2010 |
| WO | WO 2010/124117 | 10/2010 |
| WO | WO 2015039039 | 3/2015 |
| WO | WO 2015/063280 | 5/2015 |
| WO | WO 2015112863 | 1/2016 |
| WO | WO 2017059228 | 4/2017 |
| WO | WO 2018/031826 | 2/2018 |
| WO | WO 2019/236600 | 12/2019 |

OTHER PUBLICATIONS

Luini et al., Comparison of Radioguided excision with wire localization of occult breast lesions, Br. J. Surg, 1999, 86:522-525.

Mickle et al., Intellecutual Property and Ubiquitos RFID, Recent Patents on Electrical Engineering, 2008, 1:59-67.

Radio Frequency Identification: Opportunites and Challenges in Immpementation, Department of Commerce, 2005, Washington D.C., 38 pages.

Soon, Radio Frequency Identification History and Development, Chapt. 1, Ubiquitous and Pervasive Computing: Concepts, Methodologies, Tools, and Applications, 2010, ed. Symonds, 17 pages.

Stockman, Communication by Means of Reflected Power, Proceedings of the I.R.E., 1948, 36(10):1196-1204.

Takahata et al., Thoracoscopic surgery support system using passive RFID marker, 34th Annual International Conference of the IEEE EMBS, San Diego, CA, Aug. 28-Sep. 1, 2012, pp. 183-186.

Van Lieshout et al., RFID Technologies: Emerging Issues, Challenges and Policy Options, JRC Scientific and Technical Reports, 2007, 278 pages.

Want, RFID: A Key to Automating Everything, Scientific American, Inc., Jan. 2004, pp. 56-63.

International Search Report and Written Opinion, dated May 5, 2016, for PCT/US2015/012687, 11 pages.

International Search Report and Written Opinion for PCT/US2017/046379, dated Dec. 5, 2017, 15 pages.

Shah et al., Expanding the use of real-time electromagnetic tracking in radiation oncology, J Appl Clin Med Phys. Nov. 15, 2011; 12(4):3590.

Shantz, A Near Field Propagation Law & A Novel Fundamental Limit to Antenna Gain Versus Size. Antennas and Propagation Society International Symposium, 2005 IEEE, Jul. 3-8, 2005, Washington D.C. 4 pages.

International Search Report and Written Opinion for PCT/US2016/054738, dated Jan. 31, 2017, 9 pages.

European Supplemental Search Report for EP15740262.9, dated Sep. 18, 2017, 14 pages.

European Supplemental Search Report for EP16852699.4, dated May 10, 2019, 10 pages.

International Search Report and Written Opinion for PCT/US2019/035424, dated Oct. 24, 2019, 13 pages.

European Search Report for EP17840310.1, dated Mar. 30, 2020, 11 pages.

\* cited by examiner

SYSTEMS AND METHODS COMPRISING LOCALIZATION AGENTS

The present application is a 371 U.S. National Phase Entry of pending International Application No. PCT/US2015/012687, filed Jan. 23, 2015, which claims priority to U.S. Provisional Patent Application Ser. No. 61/931,395, filed Jan. 24, 2014, the disclosures of which are herein incorporated by reference in their entireties.

FIELD

Provided herein are systems and methods comprising localization agents. For example, provided herein are systems and methods for the placement of localization devices within biological systems and the detection of such localization devices for targeted surgeries or other medical procedures. For example, provided herein are systems comprising one or more miniature detectable devices that are placed into a target location and activated by remote introduction of a magnetic field.

BACKGROUND

A common and serious challenge for many medical procedures is the accurate localization of treatment areas. For example, the location of lesions, such as tumors that are to undergo treatment, including surgical resection, continues to present a challenge to the medical community. Existing systems are expensive, complex, time-consuming, and often unpleasant for the patient. Such issues are illustrated by the surgical treatment of breast lesions.

A common technique used in breast tumor surgery is wire localization of the lesions. Precise preoperative localization of some breast lesions is necessary before removal of the lesion. Wire localization is used to mark the location of a breast abnormality. The procedure ensures greater accuracy for a breast biopsy or lumpectomy. The surgeon typically uses the wire as a guide to the tissue that needs to be removed. Wire localization is typically conducted in the radiology department of the hospital or surgical center. Mammograms (or in some cases, ultrasound images) are taken to show the location of the breast abnormality. Patients are awake during the placement of the wire, but the breast tissue is numbed to reduce or avoid pain from the needle or the wire. It is possible to feel pressure or pulling sensations during the wire placement. Once images have been taken, and the tissue has been numbed, the radiologist will use a needle to target the breast abnormality. The tip of this needle rests in the location that the surgeon needs to find in order to remove the right tissue. A slender wire is threaded down through the needle and out of its tip, to lodge at the target tissue. The needle is removed, leaving the wire in place. With the wire in place, the patient has another mammogram, to check that the tip of the wire is properly positioned. If the wire is not in the correct place, the radiologist will reposition and re-check it, to ensure accurate placement. When the wire is finally positioned, it will be secured in place with tape or a bandage. The wire localization procedure can take about an hour, and is usually scheduled hours before biopsy or lumpectomy. Thus, the patient must often wait hours for surgery with the wire present in their body and protruding from their skin. The wire is removed, along with some breast tissue, during surgery. This process takes many hours, involves multiple imaging steps, and is inconvenient and unpleasant for the patient—as well as being expensive.

A similar type of procedure is done to localize pulmonary nodules prior to resection. In some cases where pulmonary nodules may be difficult to locate at conventional open surgery or at thoracoscopy, a hook wire, injection of visible dye, or a radionuclide is placed in or around the nodule in an attempt to improve localization prior to removal. This procedure usually takes place in the CT suite prior to the removal of the nodule. The patient is then transported to the surgical unit and the surgeon cuts down on the wire, uses a radionuclide detector, or uses visual landmarks to localize and remove the nodule.

In other types of surgeries and medical procedures, physicians may have trouble locating a target prior to removal or manipulation. Examples of this include the removal of masses, fluid collections, foreign bodies or diseased tissues. Other times, placements of catheters or other percutaneous procedures are performed either without direct visualization or with the lack of a specific guidance modality. Performing procedures without precise guidance can increase the amount of damage to normal tissues and decrease the patient's functional status.

Percutaneous biopsy is a well-accepted, safe procedure performed in virtually every hospital. Biopsy often entails placement of a co-axial guide needle through which the biopsy device is placed into the target. Many of the lesions that are removed, punctured or manipulated as described above have previously undergone successful percutaneous biopsy. The placement of the guide needle for biopsy is an opportunity to place a fiduciary or other localizing system without causing additional tissue trauma than the patient would otherwise undergo.

Many other medical devices and procedures could benefit from improved tissue localization. These include any procedure or test that is degraded by any bodily motion such as cardiac motion, respiratory motion, motion produced by the musculoskeletal system, or gastrointestinal/genitourinary motion. Examples of these include external beam radiation therapy, placement of brachytherapy seeds, imaging tests including but not limited to CT, MRI, fluoroscopy, ultrasound, and nuclear medicine, biopsies performed in any fashion, endoscopy, laparoscopic and thoracoscopic surgery and open surgical procedures.

Improved systems and methods are needed for tissue localization for medical procedures.

SUMMARY

Provided herein are systems and methods comprising localization agents. For example, provided herein are systems and methods for the placement of localization devices within biological systems and the detection of such localization devices for targeted surgeries or other medical procedures. For example, provided herein are systems comprising one or more miniature detectable devices that are placed into a target location and activated by remote introduction of a magnetic field.

In some embodiments, provided herein are localization agents (i.e., tags) comprising: a) a housing; and b) a signal source within said housing, wherein said signal source generates a detectable signal in response to an external activation event. In some embodiments, the signal is a signal that is directly detectable via human senses (e.g., without amplification): e.g., visually detectable, audibly detectible, tactilely detectable. In some embodiments, the signal is detectable by a detection device (e.g., and is not directly detectable via human senses). In some such embodiments, the signal is not provided by a contrast agent or radioactive source. In some embodiments, the signal is constant. In some embodiments, the signal is pulsed. In some embodiments, the signal is light and the signal source is an illumination source (e.g., light emitting diode (LED)). In some embodiments, the signal is sound and the signal source is an audio source. In some embodiments, the signal is physical movement (e.g., tactilely detectable) and the signal source is a movement component. In some embodiments, the signal is an irregularity or reflection in a magnetic field. In some embodiments, the signal is a harmonic. In some embodiments, the intensity of the signal is constant. In some embodiments, the intensity of the signal is varied (e.g., increasing or decreasing in intensity in response to the external activation event). This might include the distance from the event to the activation event, the intensity, amplitude or frequency of the activation event. In some embodiments, the nature of the signal changes (e.g., change in color, change in sound, change in pulsing pattern, etc.) in response to the external activation event.

In some embodiments, the signal source is an LED. In some embodiments, the LED is configured to emit light without the use of a power source (e.g., battery) within the tag. In some such embodiments, the two terminals (anode and cathode) of an LED are in contact with a coiled wire that, when in proximity to a changing magnetic field, induces a voltage and current into the coil, lighting the LED. The technology is not limited by the nature of the LED used. In some embodiments, the LED emits light in the visual spectrum. In some embodiments, the LED emits light in the ultraviolet or infrared spectrums. When a LED is switched on, electrons recombine with holes within the device, releasing energy in the form of photons. This effect is called electroluminescence and the color of the light (corresponding to the energy of the photon) is determined by the energy band gap of the semiconductor. In some embodiments, the LED comprises a lens or case (e.g., epoxy lens or case) surrounding a leadframe comprising an anvil and post. In some embodiments, the anvil comprises a semiconductor die in a reflective cavity and is connected to the post with a wire bond. The LED may be configured to produce different color effects (e.g., red, white, blue) (e.g., with $Y_3Al_5O_{12}$:Ce phosphor coating for white LED). In some embodiments, the semiconductor material is one or more of gallium arsenide, aluminum gallium arsenide, gallium arsenide phosphide, aluminum gallium indium phosphide, gallium (III) phosphide, indium gallium nitride, zinc selenide, silicon carbide (as a substrate), silicon (as a substrate), diamond, boron nitride, aluminum nitride, and aluminum gallium indium nitride. In some embodiments, the LED is a quantum dot LED. In some embodiments, the LED is a single-die LED to minimize its size profile.

In some embodiments, the localization tag comprises or consists of a ferrous pellet or particle. In some embodiments, the external detector comprises an activation coil that produces an alternating magnetic field. Two sense coils arranged symmetrically either coaxially or radially are balanced to a null output in the absence of the ferrous object. When the ferrous object is introduced within the field of detection coil sensitivity, the object creates an irregularity in the alternating magnetic field which disrupts the sense coil balance, producing a phase and amplitude shift from null. The null is restored when the ferrous object is physically equidistant to both sense coils.

In some embodiments, the localization tag comprises a self-resonant object (e.g., a small ferrite core with a wound inductor). The wound inductor possesses inter-winding capacitance that in combination with the inductance produces a high frequency resonant circuit. Detection occurs, for example, using the approach described above for the ferrous pellet or, for example, using a Grid Dip Oscillator (GDO). The GDO has a resonant circuit that radiates an electromagnetic field. When proximal to the self-resonant object of the same frequency, power transfer from the GDO to the self-resonant object induces a detectable change in the GDO power. In some embodiments, the localization tag comprises a resonant object (e.g., self-resonant object is equipped with a chip capacitor to produce resonance at a prescribed frequency). In some embodiments, the localization tag comprises a resonant or self-resonant object with a diode. A diode in combination with LC circuit produces a sub-harmonic frequency when immersed in a magnetic field of sufficient strength (imposed voltage exceeds the diode's band-gap potential). In some embodiments, the localization tag comprises a resonant object or self-resonant object with an active modulator (e.g., integrated circuit amplitude modulates resonant circuit). Detection occurs similar to a full duplex (FDX) radio frequency identification (RFID) except that the modulation pattern is a simple sub-harmonic rather than a coded binary pattern.

In some embodiments, the tag is configured for single-use. In some such embodiments, a tag can be disabled or deactivated (e.g., like an EAS tag). This is particularly useful where multiple tags are used in a procedure where individual tags are turned off to make detection of other tags easier (e.g., to avoid or reduce interference between multiple tags). In some embodiments, a burst of energy from an external device is used to disable or deactivate a tag. In other embodiments, the tag has an internal control component that, upon receiving instruction from an external device, turns the tag on or off (e.g., the tag stops "talking" temporarily or permanently).

In some embodiments, the tag has an exterior length, width, and depth, wherein the length is 30 mm or less (e.g., 20 mm or less, . . . , 10 mm or less, . . ., 9 mm or less, . . . , 8 mm or less, . . . , 5 mm or less, . . . , 3 mm or less, . . . , etc.), the width is 5 mm or less (e.g., 4 mm or less, . . . , 3 mm or less, . . . , 2 mm or less, . . . , 1 mm or less, . . . 0.5 mm or less, . . . , etc.), and the depth is 5 mm or less (e.g., 4 mm or less, . . . , 3 mm or less, . . . , 2 mm or less, . . . , 1 mm or less, . . . 0.5 mm or less, . . . , etc.).

In some embodiments, the localization tag is contained in a housing. In some embodiments, no housing is employed. In some embodiments, the housing comprises a biocompatible material. In some embodiments, the housing provides a liquid and/or gas resistant barrier separating the signal source from the exterior of the housing. In some embodiments, the housing is small, permitting administration of the tag through a needle, cannula, endoscope, catheter, or other medical device. In some such embodiments, the housing has an exterior length, width, and depth, wherein the length is 30 mm or less (e.g., 20 mm or less, . . . , 10 mm or less, . . . , 9 mm or less, . . . , 8mm or less, . . . , 5 mm or less, . . . , 3 mm or less, . . . , etc.), the width is 5 mm or less (e.g., 4 mm or less, . . . , 3 mm or less, . . . , 2 mm or less, . . . , 1 mm or less, . . . 0.5 mm or less, . . . , etc.), and the depth is 5 mm or less (e.g., 4 mm or less, . . . , 3 mm or less, . . . , 2 mm or less, . . . , 1 mm or less, . . . 0.5 mm or less, . . . , etc.). The housing can be of any desired shape. In some embodiments, the housing is cylindrical along the length axis. In some embodiments, the housing is shaped like a grain of rice (e.g., cylindrical with rounded ends). In some embodiments, the housing is shaped like a pillar (e.g., cylindrical with flat ends). In some embodiments, the housing is polygonal along the length axis (e.g., triangular, square, rectangular, trapezoidal, pentagonal, etc., in cross-section). In some embodiments the housing has struts or other fasteners to keep the device in place, avoiding migration in tissue. These struts may deploy upon placement in tissue. In some embodiments the fastener may be a biocompatible material that bonds with surrounding tissue.

In some embodiments, the housing is a single uniform component synthesized around the interior components of the tag. In other embodiments, the housing is made of two or more separate segments that are sealed together after introduction of the interior components of the tag.

In some embodiments, the localization tag is completely or partially covered in a coating. In some embodiments, the coating comprises a biocompatible material (e.g., parylene-C, etc.).

In some embodiments, the tag does not comprise any power source. For example, in some embodiments, the signal is generated from the signal source in response to a magnetic field as the activation event (i.e., electromagnetic induction).

In some embodiments, the tag comprises a radio-frequency identification (RFID) chip (e.g., in a housing). In some embodiments, the RFID chip comprises a radio-frequency electromagnetic field coil that modulates an external magnetic field to transfer a coded identification number and/or other coded information when queried by a reader device. In some embodiments, the RFID chip collects energy from an EM field generated by the activating device (or other device) and then acts as a passive transponder to emit microwaves or UHF radio waves. In some embodiments, a reader (which can be part of the activation device or another device) sends a signal to the RFID chip and reads its response. In some embodiments, the reader is a hand-held device that comprises a computer system RFID software or RFID middleware. In some embodiments, the RFID chip is read-only. In other embodiments, it is read/write. The technology is not limited by the nature of the information provided by the RFID chip. In some embodiments, the information includes a serial number, lot or batch number, time information (e.g., production date; surgery date; etc.); patient-specific information (e.g., name, family history, drugs taken, allergies, risk factors, procedure type, gender, age, etc.); procedure-specific information; etc. The technology is not limited by the frequency used. In some embodiments, the RFID frequency is in the 120-150 kHz band (e.g., 134 kHz), the 13.56 MHz band, the 433 MHz band, the 865-868 MHz band, the 902-928 MHz band, the 2450-5800 MHz band, or the like. In some embodiments, the RFID chip is incorporated with browser-based software to increase its efficacy. In some embodiments, this software allows for different groups or specific hospital staff, nurses, and patients to see real-time data relevant to the tag, procedure, or personnel. In some embodiments, real-time data is stored and archived to make use of historical reporting functionality and to prove compliance with various industry regulations. In some embodiments, the RFID chip reports sensor data (e.g., temperature, movement, etc.). In some embodiments, the RFID chip contains or collects information that is read at a later time (after surgery). In some embodiments, information is reviewed during surgery. For example, a message may be provided to the surgeon (e.g., "the chip is just to the left of the tumor") to assist in guiding the surgeon (e.g., optimizing removal of a tumor with the appropriate margins).

In some embodiments, the tag consists of or consists essentially of the signal source and the housing or the signal source, the housing, and the RFID chip.

In some embodiments, the tag (e.g., via the chip) emits an ultrasound signal (e.g., gray scale, spectral, or color Doppler) such that the signal is detectable by an ultrasound probe or a hand-held Doppler unit.

In some embodiments, a tag is heated during a procedure (e.g., via exposure to an external energy source). In some such embodiments, heating may be used to assist in coagulation or precoagulation of tissue or to provide thermotherapy (see e.g., U.S. Pat. Publ. No. 2008/0213382, herein incorporated by reference in its entirety). Heating may also be used to improve the efficacy of radiation therapy.

In some embodiments, a magnetic field and/or other sensing modality is provided by a remote activating device. In some embodiments, the remote activating device causes the activation event when in proximity (e.g., within a meter, . . . , 0.5 meters, . . . , 0.3 meters, . . . , 0.2 meters, . . . , 0.1 meters, . . . , 0.05 meters, . . . , etc.) to the tag. In some embodiments, the intensity of the signal increases with closer proximity of the activating device and the tag. In some embodiments, the tag does not comprise any energy storage devices (e.g., battery, capacitor, etc.).

In some embodiments, the remote activating device employs an unmodulated constant frequency activation (i.e., the activation signal has constant amplitude and frequency). In some embodiments, the localization tag produces an irregularity in the activation field. The sensing method detects a shift in either amplitude or frequency induced by the tag's presence.

In some embodiments, the remote activating device employs an unmodulated swept frequency (i.e., the activation signal has constant amplitude and swept frequency between two endpoints). Such devices find use with resonant-type tags such that a detectable change in the activation signal's amplitude occurs when the transmitted frequency coincides with the tag's resonant frequency.

In some embodiments, the remote activating device employs a pulsed frequency (i.e., the activation signal comprises brief excitation pulses at a periodic frequency, which may be comprised of two closely-related frequencies whose sum or difference is the response frequency of the tag). The pulsed activation produces a post-pulse sinusoidal decay signal. A tag alters the characteristic of the decaying signal, either in amplitude or time.

In some embodiments, the remote activating device comprises a hand-held component. In some embodiments, the hand-held component is lightweight to allow a surgeon to hold and manipulate the component over the course of a procedure (e.g., 5 kg or less, 4 kg or less, 3 kg or less, 2 kg or less, 1 kg or less, 0.5 kg or less, 0.25 kg or less, or any range therein between, e.g., 0.5 to 5 kg, 1 to 4 kg, etc.). In some embodiments, the hand-held component is shaped like a wand, having a proximal end that is held by the physician and a distal end that is pointed towards the treated subject or tissue harboring the tag. In some embodiments, the hand-held component is shaped like an otoscope, having a distal end that terminates at an angle (e.g., right angle) from the body of the component.

In some embodiments, the remote activating device comprises an antenna that generates a magnetic field. In some embodiments, the remote activating device has only a single antenna (i.e., is monostatic). In some embodiments, the remote activating device has only two antennas (i.e., is bistatic).

In some embodiments, where a wand or other lightweight or hand-held component is used, the wand or other light-weight or hand-held component may only contain a receive coil to detect signal associated with the presence of, direction of, or distance of the tag. In such embodiments, other components of the remote activating device are located outside of the wand. For example, transmission coils, radio-frequency generators and/or receivers, microprocessors, displays, and power supplies may all be located outside of the wand (e.g., in a rack, in another component that is mounted near the physician or subject, or any other desired location). In some embodiments, one or more of these components, all of them, or all but one or more of them, is included in the wand or other light-weight or hand-held component. Where such items are included, it is desirable to use light-weight items (e.g., light weight batteries as a power source).

In some embodiments, the magnetic field of the remote activating device is controlled by a processor running a computer program. In some embodiments, the remote activating device comprises a display or user interface that allows the user to control the remote activating device and/or monitor its functions while in use. In some embodiments, the remote activating device provides a visual, audio, numerical, symbol (e.g., arrows), textual, or other output that assists the user in locating the tag or identifying the distance to or direction of the tag from the remote activating device. For example, in some embodiments, a series of lights (LEDs) (e.g., 5 lights) is presented on the body of the wand, which are lit to indicate proximity or direction to the tag. In some embodiments, the user has control over the strength of the magnetic field produced by the remote activating device. In some embodiments, internal algorithms embodied in the software control the magnetic field. In some embodiments, the user may select one or more algorithms from a menu. In some embodiments, algorithms reduce or increase the sensitivity of the remote activating device based on its distance from the tag.

In some embodiments, an image from an imaging component is associated with data collected by the remote activating device. In some such embodiments, a user display provides an image of the tissue from the subject (e.g., obtained from MRI, CT, ultrasound, or other imaging modality) and overlays information about the location of the tag, the remote activating device, and/or a surgical tool used by the surgeon.

In some embodiments, the remote activating device comprises a lock-in amplifier. In some embodiments, the lock-in amplifier is configured for narrow-band detection to provide an omnidirectional detection system for determining location of the tag. In some embodiments, a modulating signal is employed and a higher harmonic caused by nonlinearity by the tag is detected. For example, a 40 kHz signal may be provided and the system looks for a $2^{nd}$ harmonic of 80 kHz generated when the tag is present. The nonlinearity may be a semiconductor diode junction excited by current flowing through a coil of the tag.

In some embodiments, as an alternative to use of a lock-in amplifier, cavity ringdown is employed. Temporal pulses are emitted and the detector looks for resonator decay over time. Not only is the phase and frequency of the ringdown signal specific to the particular tuning of the tag, but also the exponential decay (to a given threshold) of the ringdown signal's envelope is a relative indicator of the tag's distance from the excitation source.

In some embodiments, the remote activating device comprises an excitation coil that is located in a separate component from the hand-held detector. In some embodiments, the excitation coil is provided in a patch or pad that is placed on the patient or on the operating table. In some embodiments, where the system is used to locate breast tumors, the patch encircles the treated breast or is placed otherwise near the breast. In some embodiments, a pad containing the excitation coil is placed beneath the patient. In such embodiments, a large coil or multiple coils are employed. The excitation coil(s) may comprise or consist of several turns of a flat conductor patterned on a dielectric substrate, or may comprise or consist of magnet wire wound around a suitable mandrel; the coil is powered by an external frequency source, and the magnetic field emanating from the coil penetrates the patient's body to excite the tag, whose emissions (in some embodiments at a higher harmonic of the excitation or in some temporal or spectral combination unique to the tag) are detected by the wand.

In some embodiments, the excitation coil or coils are contained in a belt that is placed around the subject or a portion of the subject. In some embodiments, the external excitation coil may further be used for other aspects of the patient case, such as for radiotherapy.

In some embodiments, the remote activating device emits light (e.g., laser light).

In some embodiments, remote activating device is configured for single use (e.g., is disposable).

In some embodiments, the remote activating device is attached to or integrated with a surgical device, such as an electrosurgical device (e.g., electrocautery device such as a BOVIE device), cutting device, ablation device, or the like. A single housing may contain all components of the remote activating device and the surgical device. Alternatively, a bracket or other component is used to connect a component of a remote activating device (e.g., wand) to a surgical device. In some embodiments, a holder is used to mount both the electrosurgical device and the remote activating device together. In some embodiments, the remote activating device or a component thereof is attached to or integrated into another type of medical device that is used in the desired surgical procedure (e.g., clamps, endoscopes, bronchoscopes, extended bronchoscopes, dissection tools, lasers, laparoscopes, thoracoscopes, etc.).

Further provided herein are systems comprising the above tags and remote activating devices. For example, systems may comprise the tag and the activating device. Systems may further comprise other hardware (e.g., RFID reader), software, instructions, medical devices (e.g., cutting tools, imaging devices, tissue ablation devices, syringes, introduction needles/cannulas/endoscopes, sterilization components, etc.), pharmaceuticals, or other components useful, necessary, or sufficient for conducting a procedure with the tag. In some embodiments, the system comprises a computer that provides command and control functions for the tag and/or activating device. In some embodiments, the software collects and analyzes procedure data, information from an RFID chip, or other information generated during a procedure using the tag. In some embodiments, a computer comprises a display for displaying information to the treating physician, radiologist, patient, or other personnel involved in a procedure.

In some embodiments, provided herein are methods for localizing a tissue region of a patient, comprising: a) placing a tag (or tags) as described above into a subject (e.g., human, non-human animal, etc.); and b) localizing the tag by detecting signal (e.g., by continuous feedback or at one or more non-continuous time points). In some embodiments, the signal is generated by use of an activating device remote from the tag (e.g., located outside of the patient). In some embodiments, the tag signal has on and off modes and the activating device activates the on mode. As such, the tag provides a beacon for identifying a body region to assist in medical procedure. In some embodiments, a plurality of tags is placed in the subject. Use of a plurality of tags (e.g., in different planes relative to a target tissue) facilitates multi-dimensional (e.g., three dimensional) localization of lesions. In some embodiments two or more of the tags have different detectable properties from each other. For example, in some embodiments, each tag has a unique imbedded code or produces a unique harmonic.

The tag is not limited to placement within a particular body region, body part, organ, or tissue. For example, in some embodiments, the tag is placed in the cephalic, cervical, thoracic, abdominal, pelvic, upper extremities, or lower extremities region of the body. In some embodiments, the tag is placed within an organ system, such as the skeletal system, muscular system, cardiovascular system, digestive system, endocrine system, integumentary system, urinary system, lymphatic system, immune system, respiratory system, nervous system or reproductive system. In some embodiments, the tag is placed within an organ. Such organs may include the heart, lungs, blood vessels, ligaments, tendons, salivary glands, esophagus, stomach, liver, gallbladder, pancreas, intestines, rectum, anus, hypothalamus, pituitary gland, pineal gland, thyroid, parathyroids, adrenal glands, skin, hair, fat, nails, kidneys, ureters, bladder, urethra, pharynx, larynx, bronchi, diaphragm, brain, spinal cord, peripheral nervous system, ovaries, fallopian tubes, uterus, vagina, mammary glands, testes, vas deferens, seminal vesicles, and prostate. In some embodiments, the tag is placed within tissues, such as connective, muscle, nervous, and epithelial tissues. Such tissues may include cardiac muscle tissue, skeletal muscle tissue, smooth muscle tissue, loose connective tissue, dense connective tissue, reticular connective tissue, adipose tissue, cartilage, bone, blood, fibrous connective tissue, elastic connective tissue, lymphoid connective tissue, areolar connective tissue, simple squamous epithelium, simple cuboidal epithelium, simple columnar epithelium, stratified epithelium, pseudostratified epithelium, and transitional epithelium.

In some embodiments, the tissue region where the tag is located comprises a lesion. In some embodiments, the lesion is a tumor or a tissue region identified as being at risk for forming a tumor. In some embodiments, the lesion is fibrotic tissue. In some embodiments, the lesion is an inflamed or infected region. In some embodiments, the tag may be placed within a lumen to detect function or other process of the organ or provide localizing information. For example, the tag could be swallowed, or placed into a hollow organ via endoscopy. In some embodiments, the tissue region is healthy tissue.

In some embodiments, the tag is placed within a solid tumor. Examples of solid tumors into which the tag may be placed include carcinomas, lymphomas, and sarcomas, including, but not limited to, aberrant basal-cell carcinoma, acinar cell neoplasms, acinic cell carcinoma, adenocarcinoma, adenoid cystic carcinoma, adenoid/pseudoglandular squamous cell carcinoma, adnexal neoplasms, adrenocortical adenoma, adrenocortical carcinoma, apudoma, basal cell carcinoma, basaloid squamous cell carcinoma, carcinoid, cholangiocarcinoma, cicatricial basal-cell carcinoma, clear cell adenocarcinoma, clear cell squamous-cell carcinoma, combined small cell carcinoma, comedocarcinoma, complex epithelial carcinoma, cylindroma, cystadenocarcinoma, cystadenoma, cystic basal-cell carcinoma, cystic neoplasms, ductal carcinoma, endometrioid tumor, epithelial neoplasms, extramammary Paget's disease, familial adenomatous polyposis, fibroepithelioma of Pinkus, gastrinoma, glucagonoma, Grawitz tumor, hepatocellular adenoma, hepatocellular carcinoma, hidrocystoma, Hurthle cell, infiltrative basal-cell carcinoma, insulinoma, intraepidermal squamous cell carcinoma, invasive lobular carcinoma, inverted papilloma, keratoacanthoma, Klatskin tumor, Krukenberg tumor, large cell keratinizing squamous cell carcinoma, large cell nonkeratinizing squamous cell carcinoma, linitis plastica, liposarcoma, lobular carcinoma, lymphoepithelial carcinoma, mammary ductal carcinoma, medullary carcinoma, medullary carcinoma of the breast, medullary thyroid cancer, micronodular basal-cell carcinoma, morpheaform basal-cell carcinoma, morphoeic basal-cell carcinoma, mucinous carcinoma, mucinous cystadenocarcinoma, mucinous cystadenoma, mucoepidermoid carcinoma, multiple endocrine neoplasia, neuroendocrine tumor, nodular basal-cell carcinoma, oncocytoma, osteosarcoma, ovarian serous cystadenoma, Paget's disease of the breast, pancreatic ductal carcinoma, pancreatic serous cystadenoma, papillary carcinoma, papillary hidradenoma, papillary serous cystadenocarcinoma, papillary squamous cell carcinoma, pigmented basal-cell carcinoma, polypoid basal-cell carcinoma, pore-like basal-cell carcinoma, prolactinoma, pseudomyxoma peritonei, renal cell carcinoma, renal oncocytoma, rodent ulcer, serous carcinoma, serous cystadenocarcinoma, signet ring cell carcinoma, signet-ring-cell squamous-cell carcinoma, skin appendage neoplasms, small cell carcinoma, small cell keratinizing squamous cell carcinoma, somatostatinoma, spindle cell squamous cell carcinoma, squamous cell carcinoma, squamous cell lung carcinoma, squamous cell thyroid carcinoma, superficial basal-cell carcinoma, superficial multicentric basal-cell carcinoma, syringocystadenoma papilliferum, syringoma, thymoma, transitional cell carcinoma, verrucous carcinoma, verrucous squamous cell carcinoma, VIPoma, and Warthin's tumor.

In some embodiments, placing the tag comprises the steps of inserting an introduction device into the subject and introducing the tag through the introduction device into the subject. In some embodiments, the introduction device is a needle, cannula, or endoscope. In some embodiments, the tag is forced through the introduction device (e.g., via physical force, pressure, or any other suitable technique) and released into the subject at the distal end of the introduction device. After the tag is placed, the introduction device is withdrawn, leaving the tag at the desired location with the subject. In some embodiments, the introduction of the tag is guided by imaging technology.

In some embodiments, multiple tags are placed into the subject. The tags may be of identical type or may differ (e.g., differ in signal type). The tags may be placed in proximity to one another or at distant locations. Multiple tags are used, in some embodiments, to triangulate the location intended for medical intervention.

In some embodiments, the tags are further used as fiducials for radiotherapy (or other targeted therapy). The location of the tags is identified with an external reader and used to place, for example, laser light on the skin surface exactly where the chip is located. This eliminates the need to use X-ray, CT, or fluoroscopy to see the fiducials. This also decreases or eliminates the need to put skin markers (e.g., tattoos) on patients. This also helps in respiratory compensation as the fiducial moves up and down with a tumor in the lung or abdomen. Therefore, one can conduct real-time radiation only when the tumor is on the correct position and decrease damage to the background tissue (e.g., avoid burning a vertical stripe in the patient as the tumor moves up and down). The use as fiducials for director therapy (e.g., radiation therapy) also all enhances triangulation as depth information (based on signal strength) assists in localization of the tumor to minimize collateral damage.

In some embodiments, the tag comprises a fixing component on the outer surface (e.g., of the housing, if present) to anchor the tag in the desired location. In some embodiments, the fixing component is a hook, barb, or other physical extension. In some embodiments, the fixing component is deployable upon placement. In some embodiments, the fixing component is a textured surface. In some embodiments, the fixing component is an adhesive.

It will be appreciated that the systems and methods described herein may be applied to other uses, including non-medical uses. The technology finds use in any situation where localization of a tag is desired, including, but not limited to, surgical procedures, diagnostic procedures, veterinary procedures, food analysis, industrial applications, and environmental applications.

Definitions

As used herein, the terms "processor" and "central processing unit" or "CPU" are used interchangeably and refer to a device that is able to read a program from a computer memory (e.g., ROM or other computer memory) and perform a set of steps according to the program.

As used herein, the terms "computer memory" and "computer memory device" refer to any storage media readable by a computer processor. Examples of computer memory include, but are not limited to, RAM, ROM, computer chips, digital video discs (DVD), compact discs (CDs), hard disk drives (HDD), optical discs, and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks, whether local or distant (e.g., cloud-based).

As used herein, the term "in electronic communication" refers to electrical devices (e.g., computers, processors, etc.) that are configured to communicate with one another through direct or indirect signaling. For example, a conference bridge that is connected to a processor through a cable or wire, such that information can pass between the conference bridge and the processor, are in electronic communication with one another. Likewise, a computer configured to transmit (e.g., through cables, wires, infrared signals, telephone lines, airwaves, etc.) information to another computer or device, is in electronic communication with the other computer or device.

As used herein, the term "transmitting" refers to the movement of information (e.g., data) from one location to another (e.g., from one device to another) using any suitable means.

As used herein, the term "subject" refers to any animal (e.g., a mammal), including, but not limited to, humans, non-human primates, companion animals, livestock, equines, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass) but for whom the stage of cancer is not known. The term further includes people who once had cancer (e.g., an individual in remission).

As used herein, the term "biopsy tissue" refers to a sample of tissue (e.g., breast tissue) that is removed from a subject for the purpose of determining if the sample contains cancerous tissue. In some embodiment, biopsy tissue is obtained because a subject is suspected of having cancer. The biopsy tissue is then examined (e.g., by microscopy; by molecular testing) for the presence or absence of cancer.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include tissue, blood products, such as plasma, serum and the like. Such examples are not however to be construed as limiting the sample types applicable to the present invention.

DETAILED DESCRIPTION

The following description illustrates aspects of the technology by focusing on specific embodiments: 1) use of a tag containing an LED light source and an RFID chip for use in breast tumor lumpectomies; and 2) use of a ferrite tag with a wand-shaped activating device for use in breast tumor lumpectomies. It should be understood that the invention is not limited to these particular embodiments.

I) System Design and Manufacture

Figure 1:
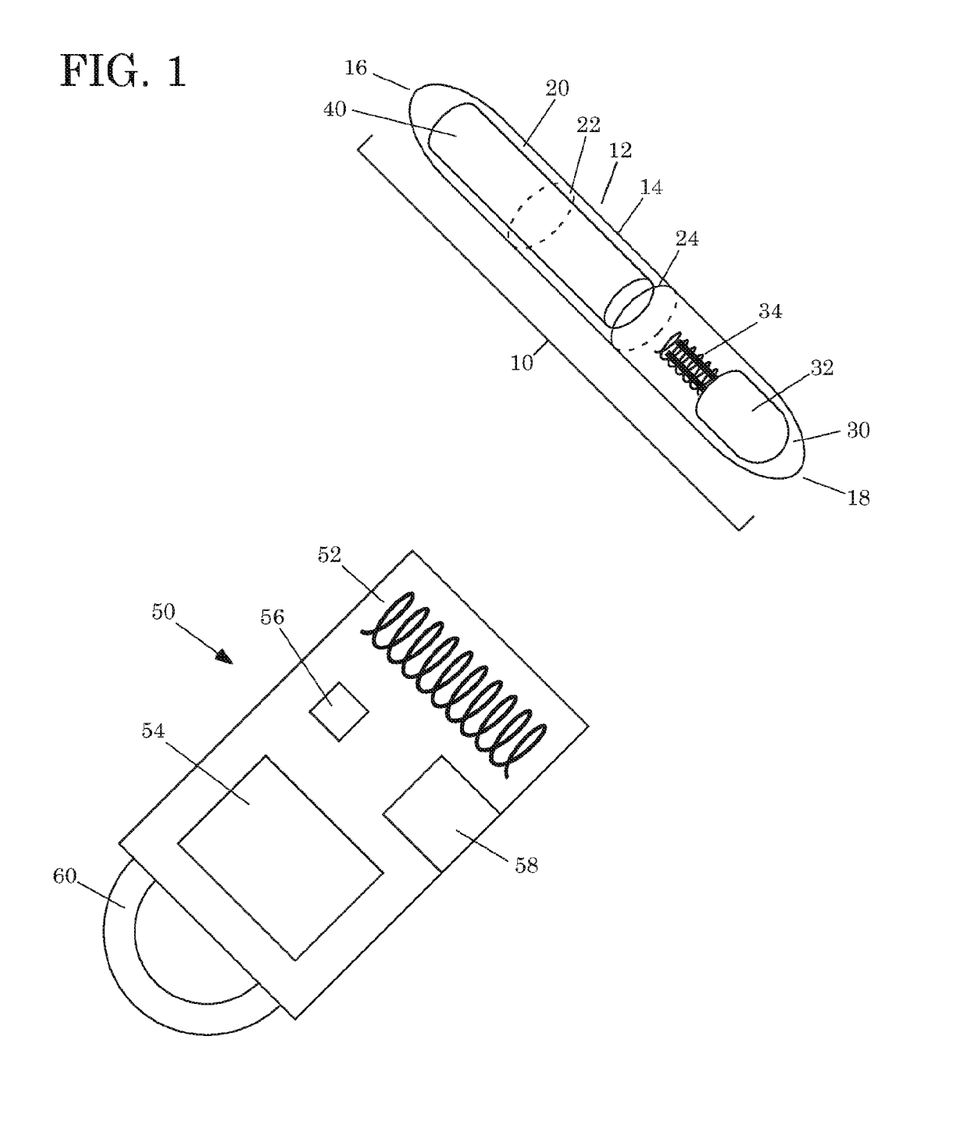
FIG. 1 shows an exemplary system comprising a tag and activating device in some embodiments of the technology.

FIG. 1 shows an exemplary system. A tag 10 comprises a housing 12 having an outer surface 14, a first end 16, a second end 18, an interior space 20, and a circular cross-sectional shape 22. The housing 12 is composed of two sections joined by a gas- and liquid-tight seal at their juncture 24.

Within the interior space 20 is an LED 30. The LED is configured for powering by inductive coupling. The LED comprises an illuminating element 32 that emits light when the LED is powered. The LED further comprises a coil region 34 comprising a coil of wire attached to the two terminals of the LED that, when in proximity to a changing magnetic field, induces a voltage and current into the coil, lighting the LED.

The interior space also comprises an RFID chip 40. The RFID chip contains a radio-frequency electromagnetic field coil that modulates an external magnetic field to transfer coded information to a reader device.

The relative dimensions of the LED 30 and RFID chip 40 are not accurately represented in the figure. In practice, LED 30 and RFID chip 40 should occupy substantially all of the interior space 20, so as to minimize the overall size of the tag.

The system further comprises an activating device 50 that provides multiple functions. The relative size of the activating device 50 compared to the tag is not accurately represented. The activating device comprises a wire coil 52 that, when powered, provides a magnetic field that, in proximity to the tag, activates the LED 30 and RFID chip 40. The activating device 50 further comprises a power source 58 that provides electrical power to the activating device 50. The power source 58 may be a battery or an electrical connection to a source of AC or DC power (an electrical cable that plugs into a remote power outlet). The activating device 50 further comprises a processor 56. The processor has multiple functions, including providing an RFID chip reading capability. The processor may further carry out any of the desired computing tasks described elsewhere herein. The activating device 50 further comprises a display 54 that displays operating parameters, data, or any other desired information to the operator. The activating device 50 further comprises a handle 60, which can have any desired format for ease of use and operability in placing the activating device 50 in proximity to the tag 10 during a medical procedure.

Figure 2:
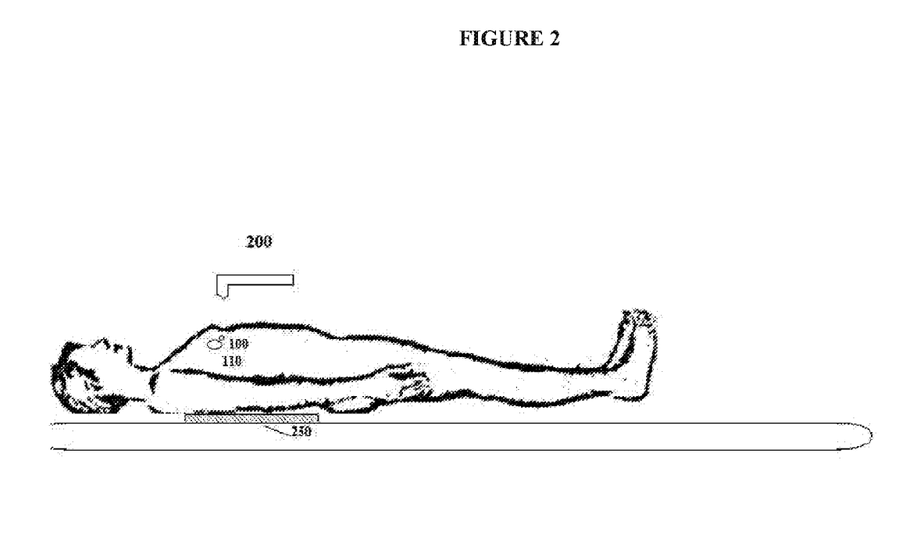
FIG. 2 shows an exemplary system comprising a ferrite tag and a wand-shaped activating device, with excitation coils located in a pad beneath the patient.

FIG. 2 shows an exemplary system. A ferrite tag 100 is placed in breast tissue near a solid tumor 110 to be surgically removed in a lumpectomy procedure.

The system further comprises a remote activating device comprising a detector wand 200 positioned above the subject and a pad 250 comprising an excitation coil 252 placed beneath the subject. The excitation coil, when powered, provides a magnetic field the emanates upwards into the patient. The ferrite tag 100 creates an irregularity in the magnetic field. The detector wand 200 comprises sense coils that detect the irregularity above the patient.

Figure 3:
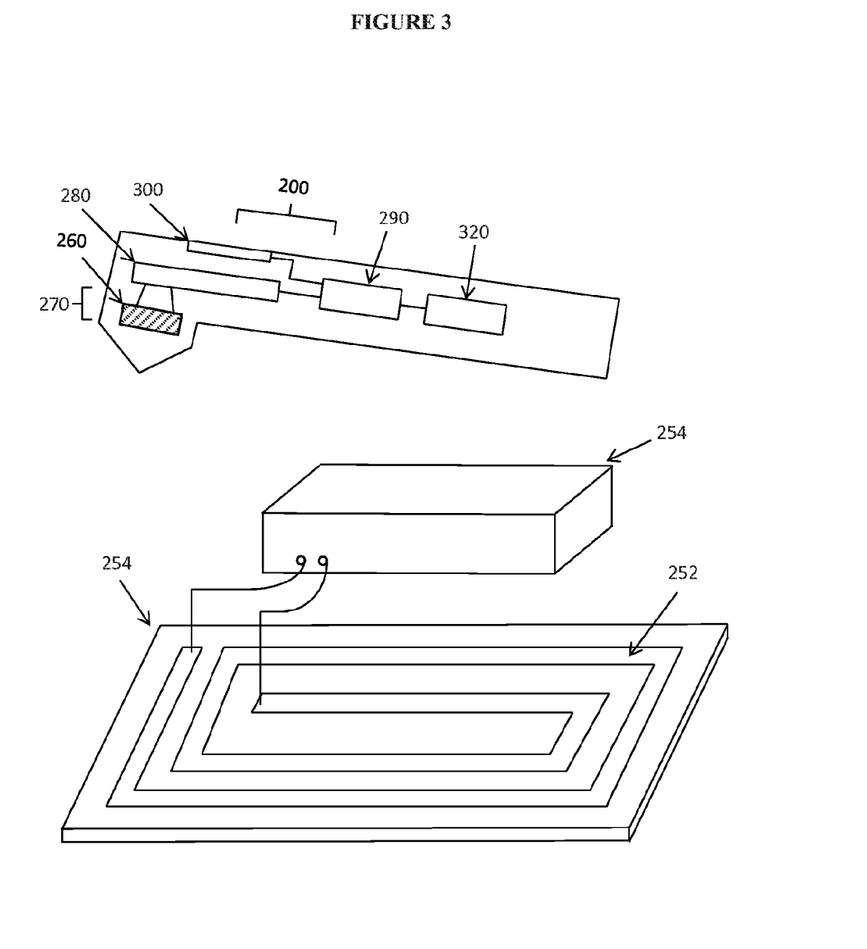
FIG. 3 shows an exemplary remote activating device with an otoscope-shaped hand-held component and a separate pad containing a magnetic field signal generator.

FIG. 3 shows a close-up of an exemplary hand-held detector wand 200 with a separate pad 250. The detector wand comprises a coil region 270 that may comprise one or more sense coils and one or more transmission coils (or both). A sense coil 260 is shown. In some embodiments, multiple sense coils (e.g., 2, 3, etc.) are employed. The sense coil 260 is connected by wires to a radiofrequency (rf) generator/receiver 280. In some embodiments, the rf generator/receiver is located outside of the hand-held component. The rf generator/receiver 280 is connected by wires to a microprocessor 290. The microprocessor 290 is also connected to a display 300 and to a power supply 320. The pad 250 containing an excitation coil 252 is connected by wires to a signal generator 254. In some embodiments, both the excitation coils and the sense coils are provided in the wand. In some embodiments, the a component comprising the excitation coil 252 is positioned on top of patient (e.g., in a pad surrounding or next to the area containing the tag.

Detection of tags of different sizes was carried out via the detection of either monostatic or bistatic $2^{nd}$ harmonics. Two targets, one 12 mm and 18 mm were employed. 30 kHz and 48 kHz frequencies were employed with detectors both axial and orthogonal to the tag. Both monostatic and bistatic modes were able to assess direction and distance to the tag, with the bistatic mode and 48 kHz frequencies providing detection at greater distances (e.g., greater than 10 cm from the tag).

In some embodiments, the components are compliant with ISO 11748/11785 standards. For example, in some embodiments, transponders are encapsulated in a biocompatible polymer or glass and a full- or half-duplex communication protocol with a reader (or interrogator) (e.g., associated with the activating device) operating at 125-134.2 kHz. In an exemplary embodiment, the reader is a modified battery-operated handheld reader compliant with the above referenced standard, e.g., one based on the Allflex Compact Reader (for specification, see allflexusa website EID Compact Reader V6). The standard reader antenna is replaced by a more direction solenoid (e.g., ferrite-core) with a pen-like form factor, and encased in a sterile sheath with a cable between the antenna and the reader. Alternatives include a reader circuitry and battery integrated in one enclosure. The tags may use materials similar to the Verichip glass-encapsulated tags that are already FDA approved for human and animal use.

In some embodiments, one or more components of the system (e.g., the activating device) is integrated into, attached to, clipped to, or otherwise associated with another medical component, including, but not limited to, a surgical cutting device, electrosurgical cutting device, or the like.

II) Tag Placement

The technology is not limited by the mode of tag placement and a wide variety of placements techniques are contemplated including, but not limited to, open surgery, laparoscopy, endoscopy, via endovascular catheter, etc. The tags may be placed by any suitable device, including, but not limited to, syringes, endoscopes, bronchoscopes, extended bronchoscopes, laparoscopes, thoracoscopes, etc. An exemplary protocol is provided below.

A patient previously identified as having a breast tumor is admitted to a medical facility. The patient is initially sent to radiology. The radiologist examines prior imaging information identifying the target tumor. The subject is administered a local anesthetic, usually lidocaine or a derivative, using a needle introduced percutaneously. The subject is positioned in an imaging device, generally either ultrasound, conventional mammography, or a stereotactic unit. The location of the tumor is determined. An introducer needle (usually 6-20 gauge) is inserted either into or just proximal to the tumor and a biopsy needle is placed through the introducer needle and a specimen is obtained using a variety of methods (suction, mechanical cutting, freezing to fix the position of the tissue followed by mechanical cutting). After the specimen is obtained and sent for pathologic examination, a 6-20 gauge tag delivery needle is inserted into the coaxial introducer needle to the tissue with the distal open end positioned at the lesion. A tag is inserted into the proximal end of the delivery needle and delivered by plunger through the opening at the distal end of the needle and into the tissue. Likewise, the tag could have been pre-positioned at the distal end of the delivery needle. Proper location of the tag is confirmed via imaging. The delivery needle is withdrawn, leaving the tag in place in the breast tissue.

This type of procedure can be performed in an analogous manner in virtually any body space, organ, or pathologic tissue with the intent of localizing that tissue or space for further diagnosis or treatment of any kind Areas of particular interest include but are not limited to the following organs, and disease processes that take place within them: brain, skull, head and neck, thoracic cavity, lungs, heart, blood vessels, gastrointestinal structures, liver, spleen, pancreas, kidneys, retroperitoneum, lymph nodes, pelvis, bladder, genitourinary system, uterus, ovaries, and nerves.

III) Surgical Procedure

The patient is placed onto an operating table with the surgical area exposed and sterilized. The surgeon is provided with the imaging information showing the location of the tumor and tag. An incision is made at the location of the entry point of the placement needle. The activating device 50 is placed in proximity to the tissue to illuminate the LED 30. The surgeon uses the light emitted from the LED to guide the direction and localization of the tumor. The activating device 50 is moved in and out of the surgical area as needed to assist in localization. Once the tumor is localized, the surgeon removes the appropriate tissue and removes the tag 10. Alternatively, the remote activating device 200 is used to detect a ferrite tag. The surgeon uses feedback from the wand detector to guide the direction and localization of the tumor.

Use of this system and procedure significantly reduces procedure cost, time, and patient inconvenience as compared to wire placement and other unguided surgeries. Use of the tag reduces the number of imaging steps required and reduces time spent in radiology and surgery. Further, the patient is not left waiting for surgery with a wire hanging out of their body. Avoidance of the wire further reduces pain or discomfort associated with the pulling on the wire.

We claim:

1. A method for activating and locating a tag that is in a tumor, or a tissue region near said tumor, of a patient, comprising:
   (a) positioning the patient with the tumor in an imaging device and determining a location of said tumor with said imaging device;
   (b) introducing the tag into said tumor, or said tissue region near said tumor, through an introduction device such that said tag is embedded in said tissue region or tumor,
   wherein said tag is at least partially covered in a biocompatible material; and wherein said tag comprises a radio-frequency identification (RFID) chip;
   (c) activating said tag by generating an alternating magnetic field at an excitation frequency with an excitation coil that is in a pad positioned beneath the patient such that said tag generates a signal at a tag frequency different than the excitation frequency in response to said alternating magnetic field; and
   (d) detecting said signal from the tag using a lock-in amplifier.

2. The method of claim 1, wherein said introduction device comprises an introduction needle.

3. The method of claim 1, wherein said introduction device comprises a cannula or an endoscope.

4. A system comprising:
   (a) a localization tag comprising a radio-frequency identification (RFID) chip, wherein said localization tag is at least partially covered in a biocompatible material;
   (b) tag delivery needle configured for delivering said localization tag into a tumor or a tissue of a patient such that said localization tag is configured to be embedded in said tumor;
   (c) a pad, comprising an excitation coil, wherein said pad is configured to be placed on an operating table and below a patient in order to generate an alternating magnetic field at an excitation frequency that penetrates the patient to excite a signal from said localization tag at a tag frequency different than the excitation frequency;
   (d) a hand-held component configured to display the presence of said localization tag; and
   (e) a lock-in amplifier to detect the signal from said localization tag.

5. The system of claim 4, wherein the tag frequency is a harmonic of the excitation frequency.

* * * * *